United States Patent [19]
Kojima et al.

[11] 4,012,258
[45] Mar. 15, 1977

[54] PROCESS FOR FORMING COLOR PHOTOGRAPHIC IMAGES

[75] Inventors: Tamotsu Kojima; Shui Sato; Wataru Fujimatsu; Hiroyuki Imamura; Takaya Endo, all of Hino, Japan

[73] Assignee: Konishiroku Photo Industry Co., Ltd., Tokyo, Japan

[22] Filed: Apr. 14, 1975

[21] Appl. No.: 568,054

[30] Foreign Application Priority Data

Apr. 12, 1974  Japan .............................. 49-41465

[52] U.S. Cl. .................................. 96/55; 96/56.5; 96/100
[51] Int. Cl.² ............................................ G03C 7/00
[58] Field of Search ...................... 96/100, 55, 56.5

[56] References Cited

UNITED STATES PATENTS

| | | | |
|---|---|---|---|
| 3,462,270 | 8/1969 | Eynde et al. | 96/100 |
| 3,623,871 | 11/1971 | Van Poucke et al. | 96/100 |
| 3,660,095 | 5/1972 | Verbrugghe et al. | 96/100 |
| 3,681,076 | 8/1972 | Skoog | 96/100 |
| 3,843,365 | 10/1974 | Van Poucke et al. | 96/100 |

Primary Examiner—J. Travis Brown
Attorney, Agent, or Firm—Haseltine, Lake & Waters

[57] ABSTRACT

Process of forming dye images using color couplers containing a monohydro-polyfluoroalkyl group.

5 Claims, No Drawings

PROCESS FOR FORMING COLOR PHOTOGRAPHIC IMAGES

This invention relates to a process for forming a dye photographic image which may be of the yellow, magenta or cyan nature. More particularly, the invention is concerned with a process for forming such dye photographic image, which is favorable in light absorption characteristic and excellent in fastness, by subjecting a light-sensitive silver halide photographic material to color development with an aromatic primary amine type developing agent in the presence of a novel yellow, magenta or cyan coupler.

Generally, the formation of a color photographic image according to subtractive color photography is carried out by subjecting a light-sensitive silver halide color photographic material to color development by use of an aromatic primary amine type developing agent in the presence of yellow, magenta and cyan couplers. In this case, silver halide particles of the photographic material, which have been exposed to light, are reduced by means of the developing agent, and the oxidation product of the developing agent, which has been formed at the same time, couples with the couplers to give a color photographic image composed of yellow, magenta and cyan dyes.

Each of the above-mentioned couplers may be incorporated into either of a silver halide photographic emulsion or a color developer. Generally, a light-sensitive silver halide photographic material, which has been incorporated with the couplers, is called an internal type photographic material, while that which is to be processed with a color developer incorporated with the couplers, is called an incorporated type photographic material.

The yellow dye photographic image of a color photograph has absorbed a blue light in the wavelength region of about 400–500 m$\mu$, the magenta dye photographic image of a color photograph has absorbed a green light in the wavelength region of about 500–600 m$\mu$, and the cyan dye photographic image of a color photograph has absorbed a red light in the wavelength region of about 600–700 m$\mu$.

For the purpose, in general, the yellow couplers used are those having an open chain active methylene group, the magenta couplers are those having a pyrazolone, pyrazolinobenzimidazole, pyrazolotriazole or indazolone nucleus, and the cyan couplers used are those having a phenolic hydroxyl group.

The couplers to be used are preferably compounds which not only form a dye image but also have such various characteristic properties that, for example, they are favorable in color developability, are high in solubility in alkalis, water and organic solvents, are high in dispersibility and stability in silver halide photographic emulsions, and can form a dye which is fast to light, heat, humidity and the like, are capable of light absorption over a desirable wavelength region and are high in transparency and color density.

Although many investigations concerning couplers having the above-mentioned properties have been made hitherto, the actual technical state is such that no desirable coupler capable of satisfying all the above-mentioned characteristic properties has been found yet.

An object of the present invention is to provide a novel coupler which has such desirable properties required for couplers as mentioned previously and which is suitable for forming a color photographic image according to substractive color photography, and to provide a process for forming a dye image desirable for a color photograph by developing a light-sensitive silver halide photographic material in the presence of one of said couplers.

The above-mentioned object can be accomplished by subjecting a light-sensitive silver halide photographic material to color development using an aromatic primary amine type developing agent in the presence of, as a yellow, magenta or cyan coupler, a compound having a monohydro-polyfluoroalkyl group which is represented by the general formula,

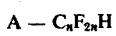

$$A - C_nF_{2n}H$$

wherein A is the residue of coupler which may be of the yellow, magenta or cyan nature and n is a positive integer of 1 to 18, provided that when A is a cyan coupler residue and n is an even number of 2 to 10, the hydrogen atom of —$C_nF_{2n}H$ being at the $\omega$-position, the terminal group of the cyan coupler residue to which the —$C_nF_{2n}H$ group is bound should not be a —NHCO group (while the —$C_nF_{2n}H$ group is bound to the side of the CO radical of the cyan coupler).

The coupler of the above-mentioned general formula (hereinafter referred to as the coupler of the present invention) is characterized by having in its molecular structure a monohydro-polyfluoroalkyl group having a hydrogen atom at the terminal, and can display various characteristic properties by virtue of the presence of said group. Further, the monohydropolyfluoroalkyl group may be introduced into any position of the coupler structure. For instance, said group may be present in a split-off group if a coupler has such split-off group which can be liberated during the development.

That is, the coupler of the present invention is favorable in solubility in water, alkalis and organic solvents, in dispersion stability in photographic emulsions, and in color developability, and gives by color development a yellow, magenta or cyan dye image which is high in maximum color density, has a light absorption in a desirable wavelength region, is favorable in transparency and is excellent in fastness to light, heat and humidity.

On the other hand, U.S. Pat. No. 2,772,162 has taught that a coupler having a perfluoroalkylcarbonamido group has such characteristic as being particularly excellent in heat resistance. The coupler of the present invention has an alkyl-group in which many fluorine atoms have substituted for hydrogens, and hence is also excellent in heat resistance. In addition to such advantage in heat resistance, however, a coupler of the present invention is specifically excellent in solubility in usual solvents for couplers, this resulting from the existence of one hydrogen atom in its molecular structure. Further, such a coupler of the invention where a monohydro-polyfluoroalkyl group is introduced into a position near the dye-forming nucleus of the coupler characteristically shifts the absorption wavelength region of the formed dye toward the longer wavelength side. Still further, a coupler of the present invention has better absorption characteristic and excellent in color reproduction when it is a yellow coupler, has better color developability with higher maximum density when it is a magenta coupler, and has particularly excellent solubility when it is a cyan coupler, all these being derived from the particular feature of the invention, that is the existence of a monohydropolyfluoroalkyl group.

The couplers of the present invention include those which are soluble in water, alkalis or oils, and those of the internal type which are to be incorporated into silver halide photographic emulsions and of the incorporated type which are to be incorporated into color developers, and the kinds thereof are decided according to the kinds of groups which are introduced into the dye-forming nuclei.

Typical examples of the yellow couplers of the present invention are shown below.

Coupler (1)

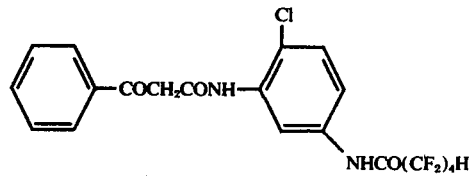

Coupler (2)

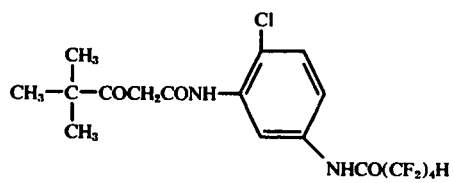

Coupler (3)

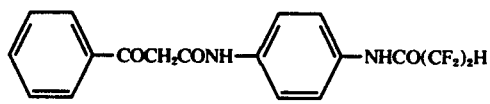

Coupler (4)

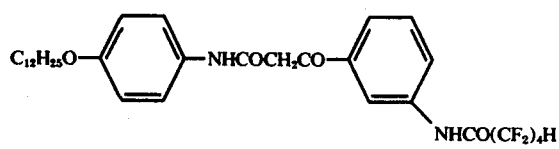

Coupler (5)

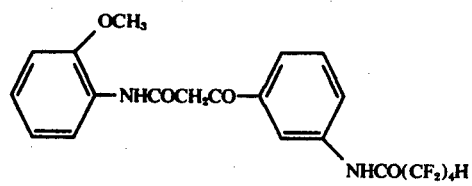

Coupler (6)

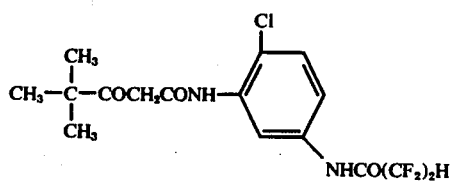

Coupler (7)

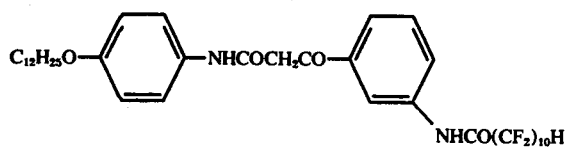

Coupler (8)

-continued
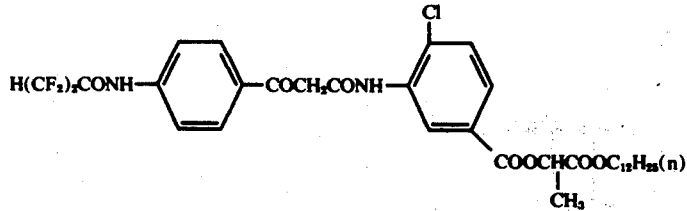
Coupler (9)
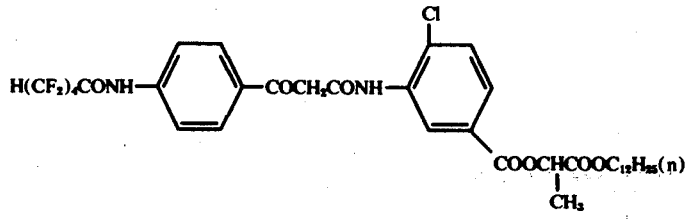
Coupler (10)
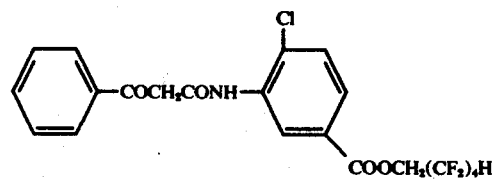
Coupler (11)
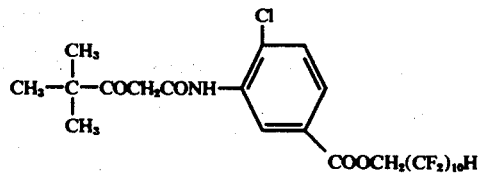
Coupler (12)
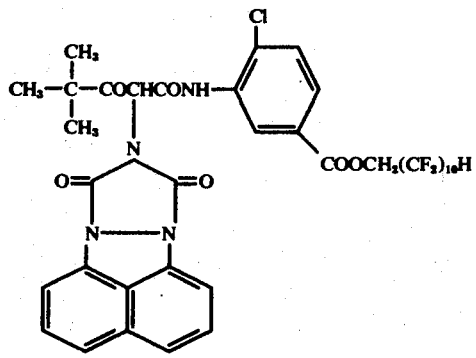
Coupler (13)
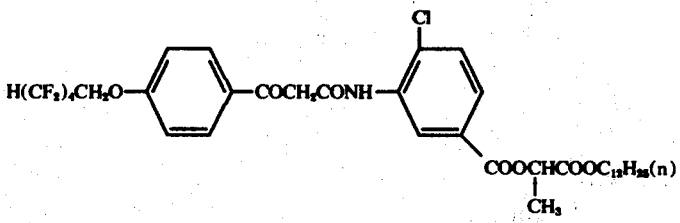
Coupler (14)

-continued
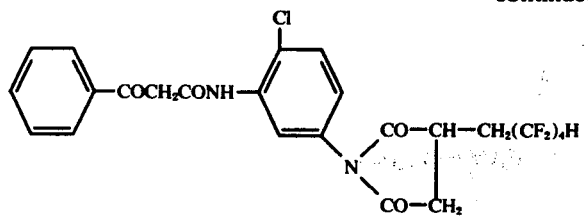
Coupler (15)
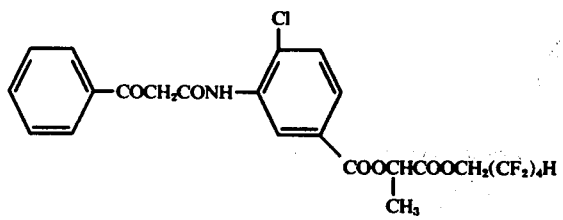
Coupler (16)
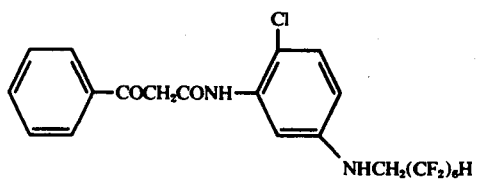
Coupler (17)
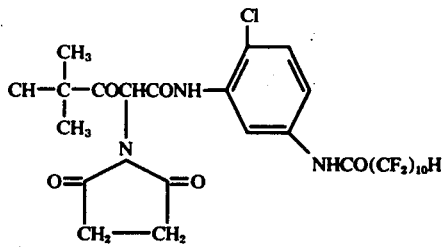
Coupler (18)
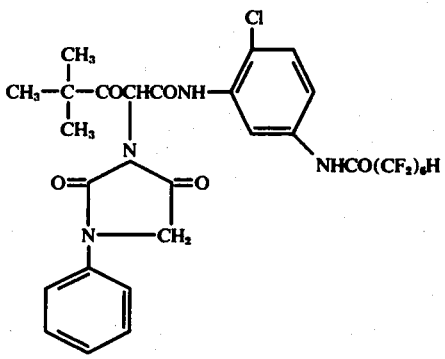
Coupler (19)
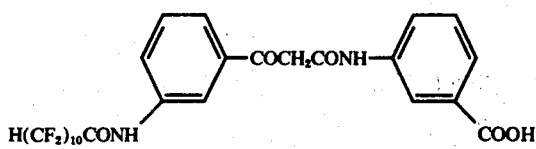
Coupler (20)

-continued
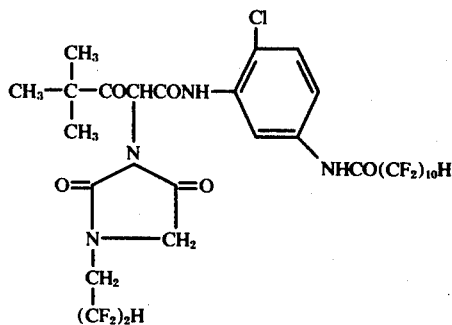
Coupler (21)
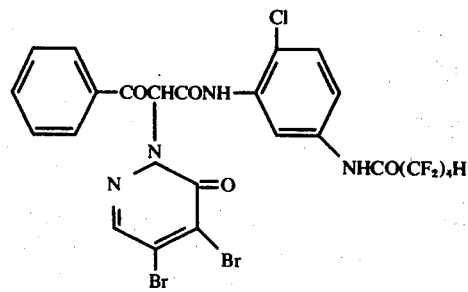
Coupler (22)
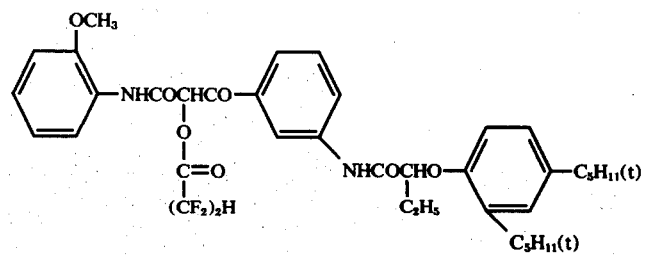
Coupler (23)
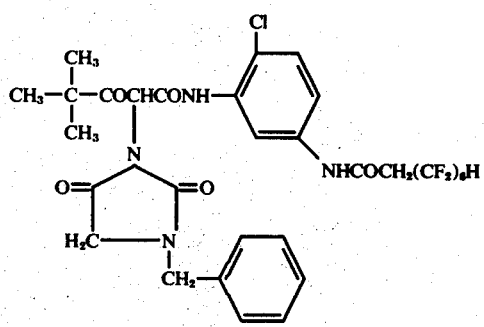
Coupler (24)
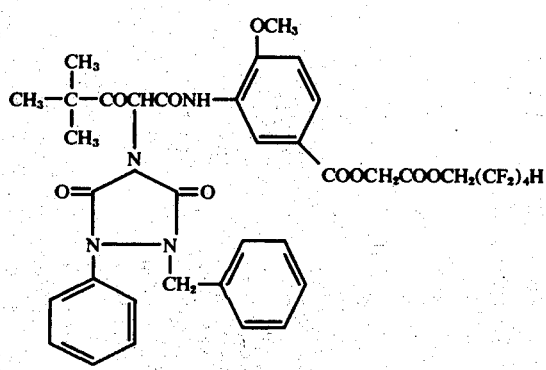

Typical examples of the magenta couplers of the present invention are shown below.
Coupler (25)
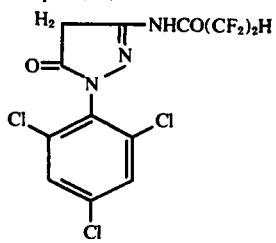
Coupler (26)
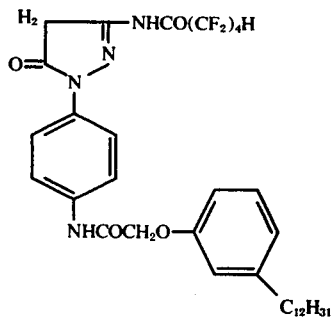
Coupler (27)
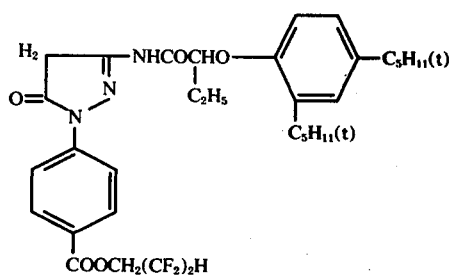
Coupler (28)
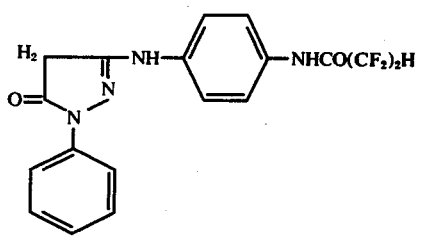
Coupler (29)
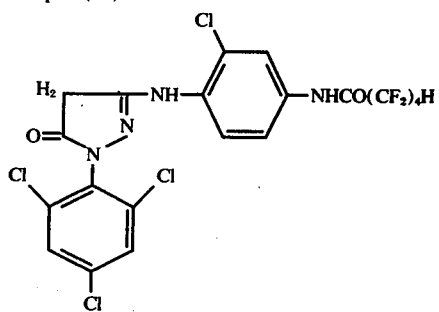
Coupler (30)

-continued
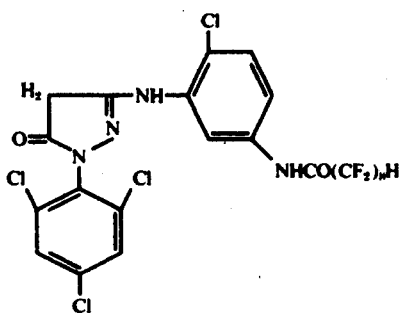
Coupler (31)
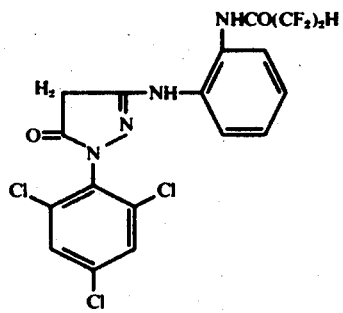
Coupler (32)
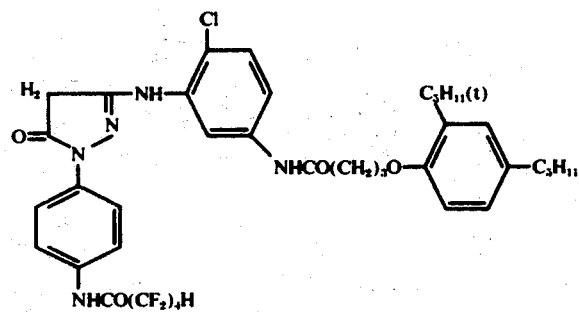
Coupler (33)
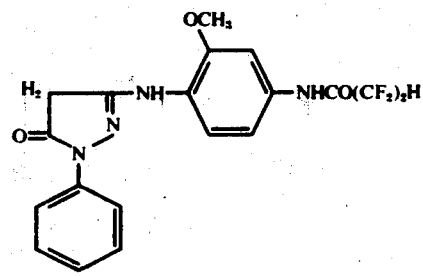
Coupler (34)
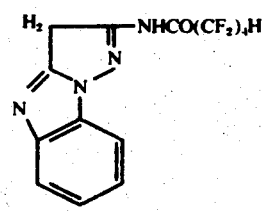
Coupler (35)

-continued
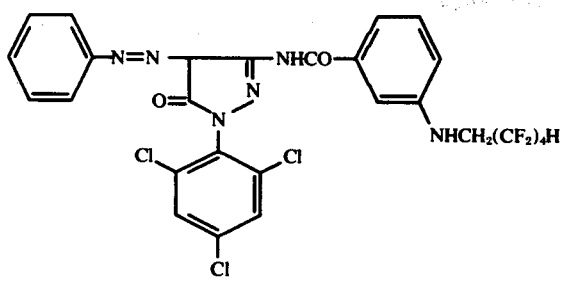
Coupler (36)
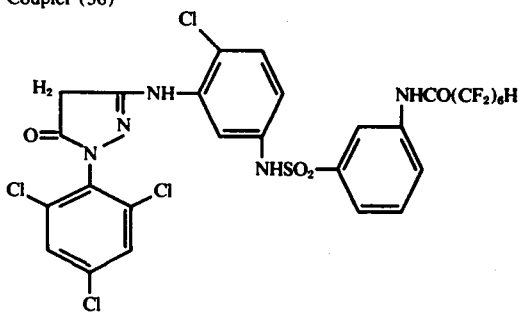
Coupler (37)
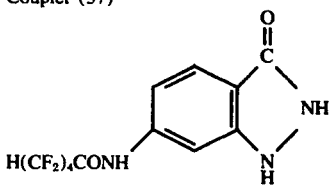
Coupler (38)
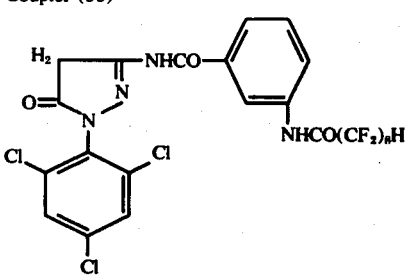
Coupler (39)
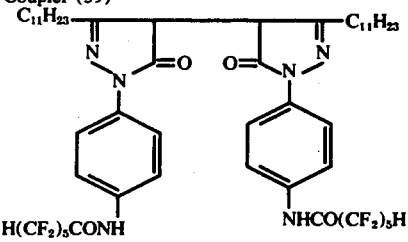
Coupler (40)
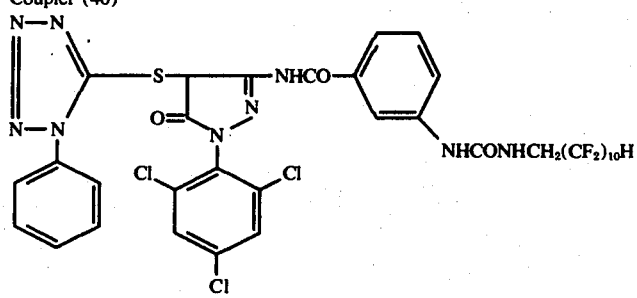

Coupler (41)
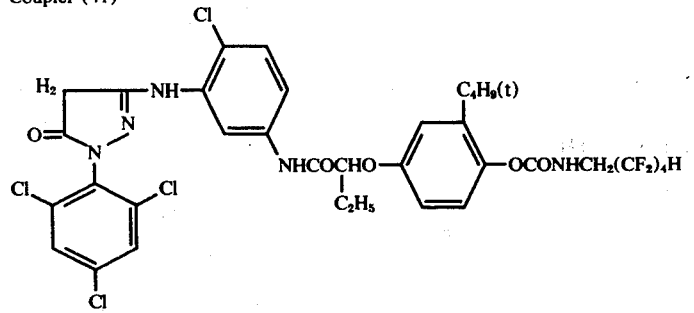
Coupler (42)
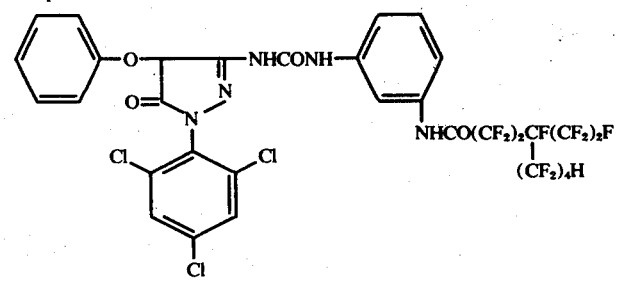
Coupler (43)
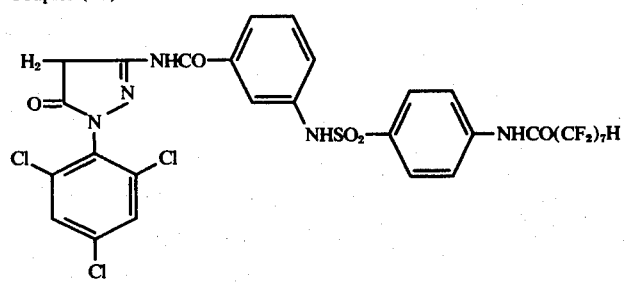
Coupler (44)
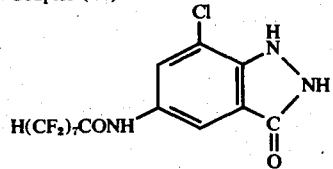
Typical examples of the cyan couplers of the present invention are shown below.
Coupler (45)
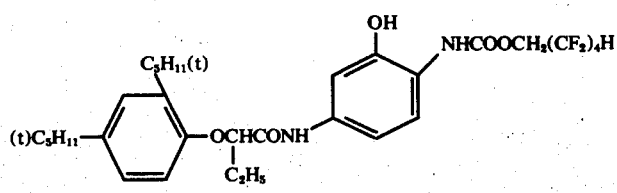
Coupler (46)
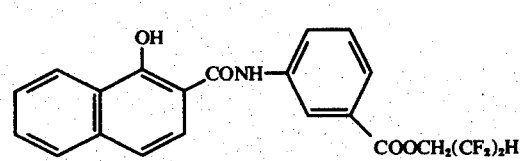
Coupler (47)

-continued
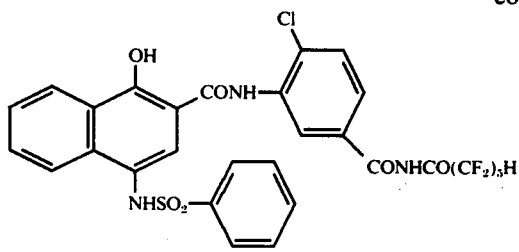
Coupler (48)
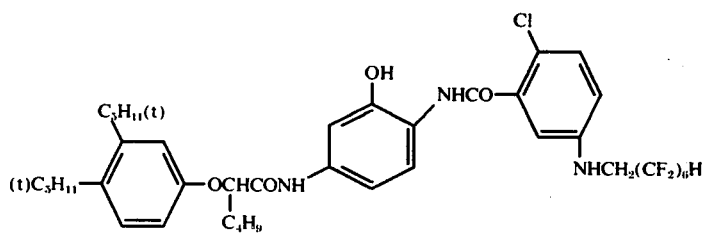
Coupler (49)
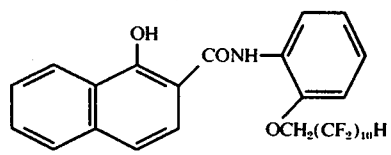
Coupler (50)
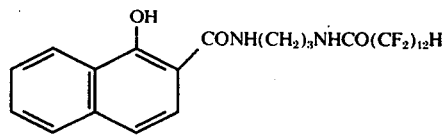
Coupler 51
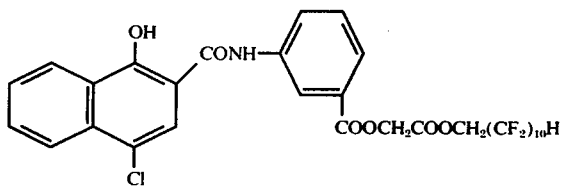
Coupler 52
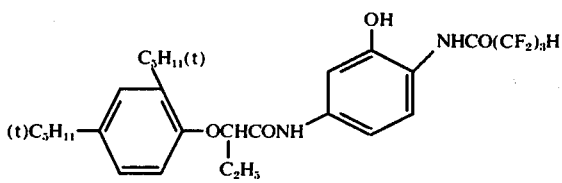
Coupler (53)
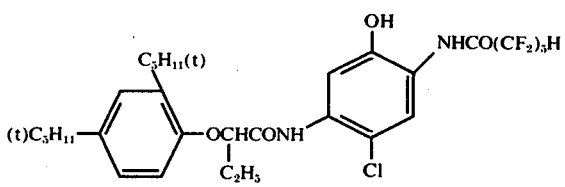
Coupler (54)

-continued
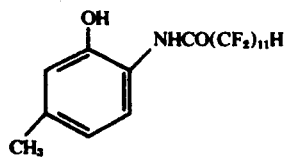
Coupler (55)
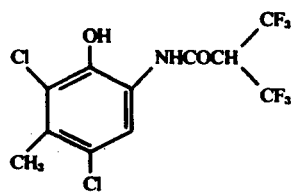
Coupler (56)
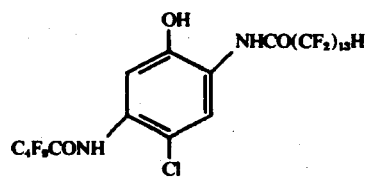
Coupler (57)
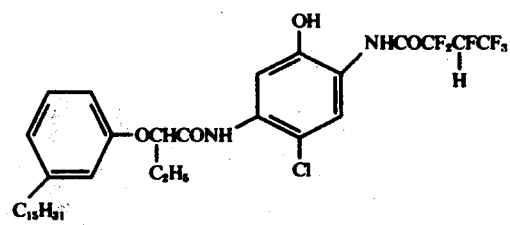
Coupler (58)
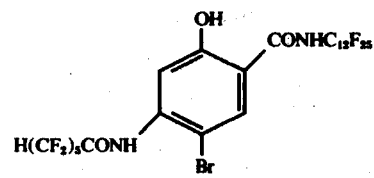
Coupler (59)
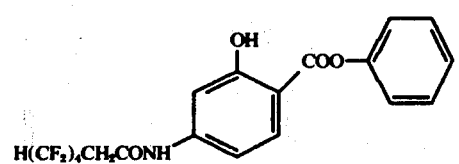
Coupler (60)
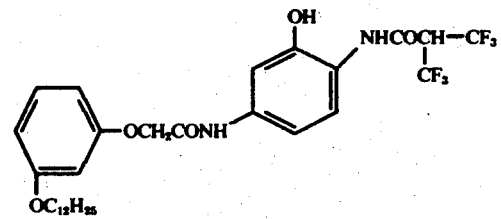
Coupler (61)
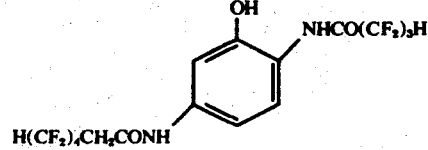

Coupler (62)
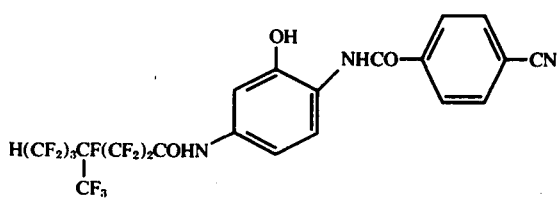
Coupler (63)
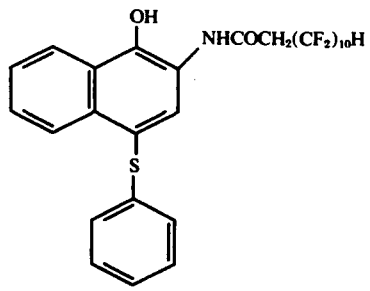
Coupler (64)
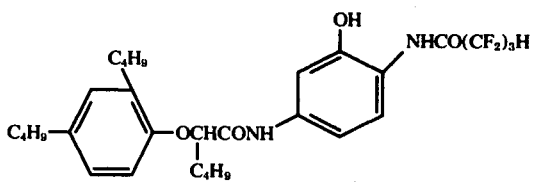
Coupler (65)
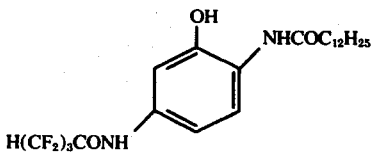
Coupler (66)
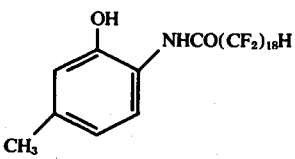
Coupler (67)
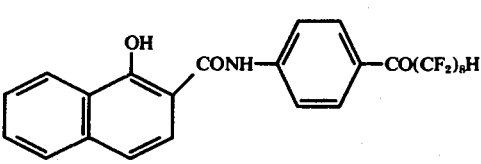
Coupler (68)
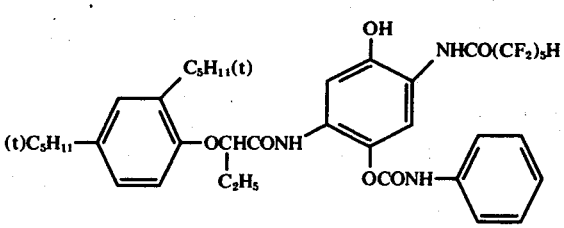
Coupler (69)

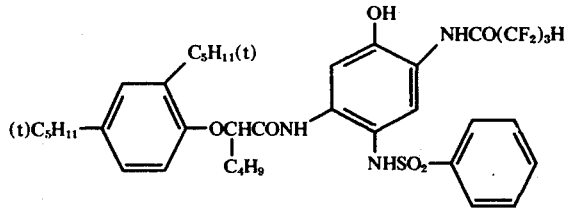
Coupler (70)
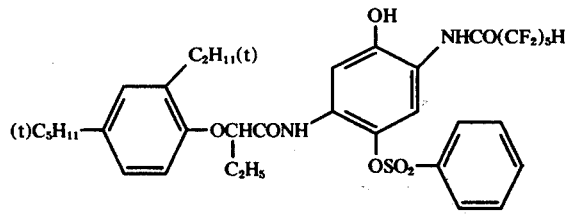
Coupler (71)
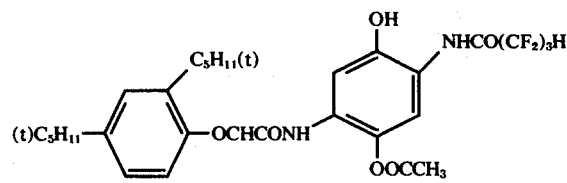
Coupler (72)
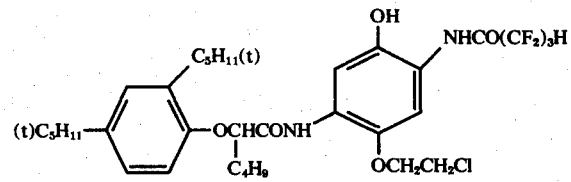
Coupler (73)
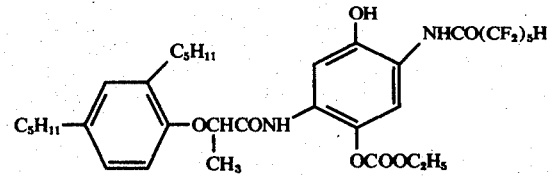
Coupler (74)
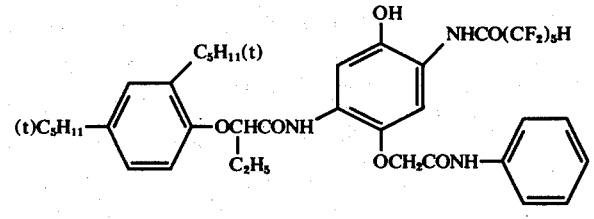
Coupler (75)
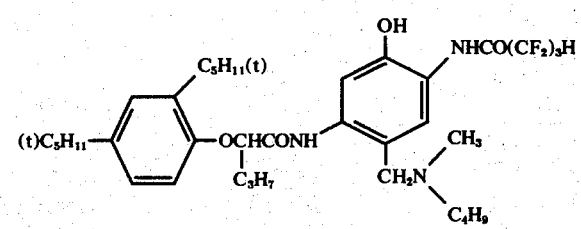
Coupler (76)

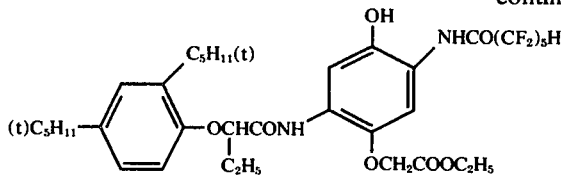

Coupler (77)

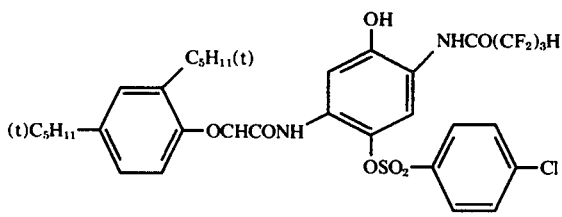

Coupler (78)

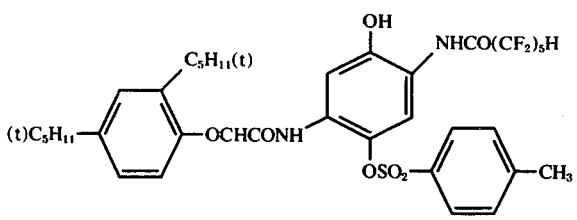

Procedures for synthesizing typical couplers of the present invention are explained below with reference to synthesis examples.

SYNTHESIS EXAMPLE 1

Synthesis of Coupler (2)

1-(1) Synthesis of ω-monohydro-octafluoropentanoyl chloride:

74 Grams of ω-monohydro-octafluoropentanoic acid (synthesized according to the method disclosed in U.S. Pat. No. 2,559,629) is gradually added dropwise into 62.4 g. of phosphorus pentachloride, and the resulting mixture is reacted at 90° C. ± 10° C. for one hour, whereby a colorless transparent liquid reaction mixture is obtained. This reaction mixture is distilled at atmospheric pressure to obtain 54 g. of the end product which is a colorless liquid having a boiling point of 89° to 93° C.

1-(2) Synthesis of the Coupler (2):

26 Grams of the ω-monohydro-octafluoropentanoyl chloride obtained in the above-mentioned step 1-(1) is added dropwise at room temperature over a period of 30 minutes to a solution comprising 27 g. of α-pivalyl-2-chloro-5-amino-acetanilide and 150 ml of $CH_3CN$, and the resulting mixture is stirred in a bath at the outside bath temperature of 70° to 80° C. for 3 hours. Subsequently, the liquid reaction mixture is concentrated and the residue is poured into a ethanol-water (1:1) solvent mixture to deposit precipitates, which are then collected by filtration and dried under reduced pressure to obtain the end product consisting of white crystals having a melting point of 133° to 135° C.

SYNTHESIS EXAMPLE 2

Synthesis of Coupler (1)

Exactly the same procedure as in 1-(1) of Synthesis Example 1 is repeated, except that 29 g. of α-benzoyl-2-chloro-5-amino-acetanilide and 26 g. of ω-monohydro-octafluoropentanoyl chloride are used. Finally, the concentrated residue is poured into a ethanol-water (1:1) solvent mixture to deposit precipitates, which are collected and dried under reduced pressure. Thereafter, the precipitates are recrystallized from carbon tetrachloride to obtain 38 g. of the end product consisting of white crystals having a melting point of 104° to 107° C.

SYNTHESIS EXAMPLE 3

Synthesis of Coupler (14)

Exactly the same procedure as in 1-(2) of Synthesis Example 1 is repeated, except that 21 g. of α-(2-chloro-3-amino)-benzoyl-4-dodecyloxyacetanilide and 13 g. of ω-monohydro-octafluoropentanoyl chloride. Finally, the concentrated residue is recrystallized from methanol to obtain 17 g. of the end product.

SYNTHESIS EXAMPLE 4

Synthesis of Coupler (25)

16.4 g of ω-monohydro-tetrafluoropropionyl chloride obtained according to the procedure similar to that of 1-(1) of Synthesis Example 1 is added to a solution comprising 27.8 g. of 1-(2,4,6-trichlorophenyl)-3-amino-5-pyrazolone, 150 ml of $CH_3CN$ and 5 ml of pyridine, and the resulting mixture is reacted by heating. The reaction mixture is poured into water to deposit crystals, which are recrystallized, after drying, from $CH_3CN$ to obtain 20 g. of the end product consisting of white crystals having a melting point of 221° to 223° C.

SYNTHESIS EXAMPLE 5

Synthesis of Coupler (30)

A mixture comprising 20.2 g. of 1-(2,4,6-trichlorophenyl)-3-(2-chloro-5-amino-anilino)-5-pyrazolone, 200 ml of $CH_3CN$ and 13.2 g. of ω-monohydro-octafluoropentanoyl chloride is reacted by heating for 3 hours. The liquid reaction mixture is concentrated and heated to dryness. The dried residue is recrystallized from a n-hexane-ethanol (4:1) solvent mixture to obtain 14 g. of the end product consisting of white crystals having a melting point of 201° to 203° C.

As mentioned previously, the couplers of the present invention include those which are soluble in water, alkalis and oils. Among the water- and alkali-soluble couplers, those which are of the type having diffusion-preventing groups can be dispersed and incorporated according to the so-called Fischer's dispersion method into silver halide photographic emulsions. Examples of the couplers belonging to this type are the aforesaid coupler (19). On the other hand, those which are of the type having no diffusionpreventing groups are incorporated into color developers and can be used for the processing of light-sensitive silver halide color photographic materials of the incorporated type. Examples of the couplers belonging to this type are the aforesaid couplers (1), (2) and (25). Further, the oil-soluble couplers are dissolved as oil-protected type couplers in high boiling point organic solvents and may be dispersed and incorporated into silver halide photographic emulsions.

For incorporation into light-sensitive silver halide photographic materials of, for example, the oil-protected type couplers among those of the present invention, there may be adopted any of the known procedures. For example, one or more of the couplers are dissolved in one, or if necessary both, of a high boiling solvent having a boiling point of more than 175° C. such as tricresyl phosphate or dibutyl phthalate, and a low boiling solvent such as butyl acetate or butyl propionate. Thereafter, the resulting solution is mixed with an aqueous gelatin solution containing a surfactent, and then emulsified by means of a high speed rotary mixer or a colloid mill to form an emulsion. This emulsion is incorporated directly into a silver halide photographic emulsion, which is then coated on a support including glass plates, synthetic resin plates, various film bases, baryta papers and polyethylene laminate papers, and is then dried to remove a major proportion of the low boiling solvent, whereby a light-sensitive silver halide photographic material can be prepared. Alternatively, the said emulsion is once set, finely cut (extruded into the form of noddles) and subsequently freed from the low boiling solvent by water-washing or the like means, and the thus treated emulsion is incorporated into said photographic emulsion, which is then coated on said support and dried, whereby a light-sensitive silver halide photographic material can be obtained.

The above-mentioned incorporation procedure is merely an example, and it is needless to say that the manner of incorporation of the coupler of the present invention is not limited to the above.

In the above case, the amount of the coupler to be incorporated into the emulsion is preferably in the range from 10 to 100 g. per mole of the silver halide, in general. However, the amount of said coupler is not always limited to said range, but may be properly varied according to the application purpose of the resulting photographic material. Further, the coupler of the present invention may be incorporated into two or more of different emulsion layers of a multi-layered light-sensitive color photographic material.

The silver halide emulsion used in the present invention may be prepared by use of any silver halide salt such as silver chloride, silver iodobromide or silver chlorobromide, and may contain a chemical sensitizer such as a sulfur sensitizer, a natural sensitizer present in gelatin, a reduction sensitizer or noble metal salts. Further, the emulsion may contain ordinary photographic additives such as, for example, antifoggant, stabilizer, anti-stain agent, anti-irradiation agent, physical property-improving high molecular weight additive, hardener, coating aid, etc., and may contain as an optical sensitizer any of carbocyanine and merocyanine dyes.

The thus obtained light-sensitive color photographic material is exposed to radiation such as $\alpha$-rays or $\beta$-rays, visible rays of ultraviolet rays, developed with a color developer containing an aromatic primary amine type compound as a developing agent, and then subjected to bleaching, desilvering and fixing to obtain an image containing a high density dye excellent in spectral absorption characteristic and durability and favorable in transparency. Obviously, the processing of a light-sensitive color photographic material containing a coupler of the present invention may also be made by using a bleach solution or a bleach-fix solution which contains as its oxidizing agent, iron chloride, potassium bichromate, potassium persulfate, potassium or the like ferricyanide, or the polyvalent cation or alkali metal complex of a water-soluble organic acid. In such processing, bleaching and fixation may be made successively or concurrently. According to the situation, bleaching may be followed by treatment with a bleach-neutralizing bath and then with a fixing bath. In all the cases, satisfactory result can be obtained. The durability of the color image can further be enhanced when the photographic material containing the coupler of the present invention is incorporated with an ultraviolet absorber of the benzophenone type, e.g. 2-hydroxy-4-dodecyloxybenzophenone, or the triazole type, e.g. 2-(2'-hydroxy-3',5'-di-tert-butylphenyl)benzotriazole.

Typical examples of the aromatic primary amine type developing agent used for development in the present invention are sulfates, sulfites and hydrochlorides of N,N-diethyl-p-phenylenediamine, N-ethyl-N-$\beta$-methanesulfonamidoethyl-3-methyl-4-aminoaniline, N-ethyl-N-hydroxyethyl-p-phenylenediamine, N-ethyl-N-hydroxyethyl-2-methyl-p-phenylenediamine and N,N-diethyl-2-methyl-p-phenylenediamine.

Further, the color developer may contain a development control agent, e.g. citrazinic acid, in addition to the aforesaid developing agent.

The present invention is illustrated in further detail below with reference to examples, but the examples are by way of illustration, and the modes of practice of the invention are, of course, not limited to the examples.

In the examples, such known couplers as shown below were used as control couplers for comparison.

Control coupler (i)

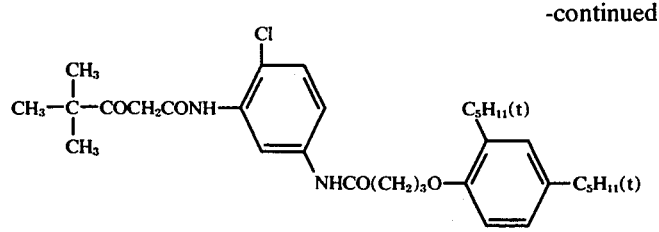

(cf. U.S.P. 3,265,506)

Control coupler (ii)

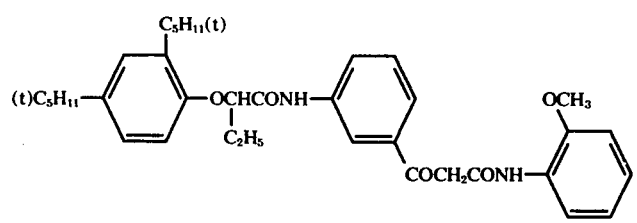

(cf. U.S.P. 2,875,057)

Control coupler (iii)

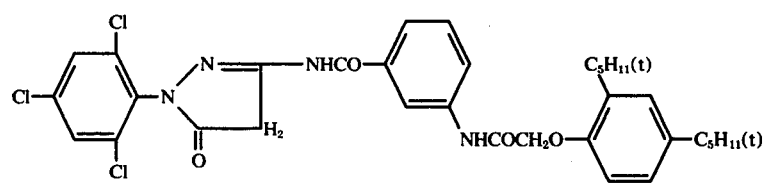

(cf. U.S.P. 2,808,420)

Control coupler (iv)

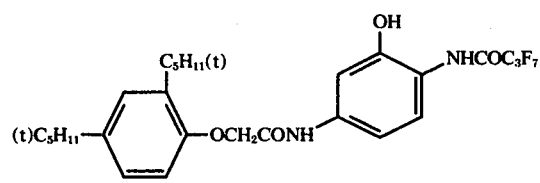

(cf. U.S.P. 2,895,826)

EXAMPLE 1

10 Grams of each of the couplers (11), (12), (15), (36), (38), (45), (48) and (52) and the control couplers (i), (ii), (iii) and (iv) was completely dissolved at 60° C. in a mixture comprising 20 ml. of dibutyl phthalate and 60 ml. of ethyl acetate. This solution was mixed with 5 ml. of a 10% aqueous solution of Alkanol B(alkylnaphthalene sulfonate, commercially available from E. I. Du Pont de Nemours & Co.) and 20 ml. of a 5% aqueous gelatin solution, and the resulting mixture was emulsified by use of a colloid mill to prepare a dispersion of each coupler.

Subsequently, each coupler dispersion was added to 500 g. of a high speed negative, gelatinous silver iodobromide emulsion (containing 6 mole% of silver iodide), which was then coated on a cellulose triacetate film base and dried to obtain twelve kinds of photographic materials each having a stable coating film which were designated Sample Nos. (1) to (12).

After exposure through an optical wedge, each sample was subjected to color development at 20° C. for 10 minutes, using a color developer of the following composition:

Composition of the color developer:
  N-Ethyl-N-β-methanesulfonamidoethyl-3-methyl-4-aminoaniline sulfate: 5.0 g.
  Anhydrous sodium sulfite: 2.0 g.
  Sodium carbonate (monohydrate): 50.0 g.
  Potassium bromide: 1.0 g.
  Sodium hydroxide: 0.55 g.
  Benzyl alcohol: 4.0 g.
  Water to make: 1,000 ml.

Subsequently, the developed sample was subjected to ordinary stopping (for 2 minutes), fixing (for 5 minutes) and water-washing (for 10 minutes), and then bleached for 5 minutes with a bleaching solution of the following composition:

Composition of the bleaching solution:
  Potassium ferricyanide: 100 g.
  Potassium bromide: 50 g.
  Water to make: 1,000 ml.

Thereafter, the sample was subjected to water-washing for 5 minutes, and then fixed at 20° C. for 5 minutes with a fixing solution of the following composition:

Composition of the fixing solution:
  Sodium thiosulfate (pentahydrate): 250 g.
  Water to make: 1,000 ml.

The sample was again subjected to water-washing for 25 minutes, and then dried to form a yellow dye image on Samples (1), (2), (3), (9) and (10), a magenta dye image on Samples (4), (5) and (11), and a cyan dye imate on Samples (6), (7), (8) and (12), respectively.

The dye image formed in each sample was measured in speed, gamma, maximum density ($D_{max}$), absorption maximum wavelength ($\lambda_{max}$) and fastness to light, heat and humidity. The results obtained were as set forth in Table 1.

In the table, the speed was represented by a relative value measured by assuming as 100 the speed of Sample (9) for yellow couplers, that of Sample (11) for magenta couplers and that of Sample (12) for cyan couplers. Further, the light fastness was represented by the percentage to the density of untreated dye of the density of residual dye after treating the sample for 16 hours by use of a Xenon Fade-O-Meter, and the heat-humidity fastness was represented by the percentage to the density of untreated dye of the density of residual dye after incubating the sample for two weeks under the conditions of 50° C. and 80%RH.

Table 1

| Sample No. | Coupler | Speed | Gamma | $D_{max}$ | $\lambda_{max}$ (mu) | Fastness Light fastness | Heat-humidity fastness |
|---|---|---|---|---|---|---|---|
| 1 | Coupler (11) | 125 | 1.10 | 2.13 | 448 | 94 | 96 |
| 2 | Coupler (12) | 150 | 1.30 | 2.51 | 448 | 95 | 97 |
| 3 | Coupler (15) | 130 | 1.33 | 2.40 | 453 | 90 | 95 |
| 4 | Coupler (36) | 132 | 1.36 | 2.48 | 540 | 95 | 99 |
| 5 | Coupler (38) | 115 | 1.27 | 2.33 | 558 | 89 | 85 |
| 6 | Coupler (45) | 160 | 1.20 | 2.70 | 665 | 96 | 95 |
| 7 | Coupler (48) | 146 | 1.22 | 2.60 | 670 | 97 | 93 |
| 8 | Coupler (52) | 135 | 1.21 | 2.56 | 680 | 95 | 95 |
| 9 | Control coupler (i) | 100 | 0.98 | 1.80 | 447 | 90 | 95 |
| 10 | Control coupler (ii) | 120 | 1.10 | 2.13 | 453 | 83 | 94 |
| 11 | Control coupler (iii) | 100 | 1.20 | 2.25 | 555 | 80 | 73 |
| 12 | Control coupler (iv) | 100 | 1.11 | 2.20 | 678 | 92 | 90 |

As is clear from Table 1, Samples (1) to (8), in which had been used the couplers of the present invention, gave dye photographic images which were more favorable in photographic properties than other samples, in which had been used the control couplers. Moreover, the images obtained were quite clear and were excellent in transparency.

EXAMPLE 2

Samples (6), (7), (8) and (12) prepared in Example 1 were individually exposed through an optical wedge, and then subjected to color development at 38° C. (for 3 minutes and 15 seconds), bleaching (for 6 minutes), water-washing (for 3 minutes), fixing (for 6 minutes and 30 seconds), water-washing (for 3 minutes) and stabilization (for 1 minute and 30 seconds) to investigate the influence derived from the difference in manner of development treatment. As the result, it was confirmed that the photographic properties of the dye image formed in each sample were the same as in Example 1.

The compositions of the color developer and bleaching solution used in this example were as follows:
Composition of the color developer:
  N-Ethyl-N-(β-hydroxyethyl)-3-methyl-4-aminoaniline hydrochloride: 5.0 g.
  Anhydrous sodium sulfite: 2.0 g.
  Sodium carbonate (monohydrate): 50.0 g.
  Potassium bromide: 1.0 g.
  Sodium hydroxide: 0.55 g.
  Water to make: 1,000 ml.
Composition of the bleaching solution:
  Iron ammonium ethylenediamine tetraacetate: 100 g.
  Diammonium ethylenediamine tetraacetate: 10 g.
  Ammonium bromide: 150 g.
  Glacial acetic acid: 10 ml.
  Water to make: 1,000 ml.

EXAMPLE 3

10 Grams of each of the couplers (8), (14), (30) and (53) and the control coupler (ii), (iii) and (iv) was completely dissolved at 60° C. in a mixture comprising 20 ml. of tricresyl phosphate and 60 ml. of ethyl acetate. This solution was mixed with 5 ml. of a 10% aqueous solution of Alkanol B and 200 ml. of a 5% aqueous gelatin solution, and the resulting mixture was emulsified by use of a colloid mill to prepare a dispersion of each coupler.

Subsequently, each coupler dispersion was added to a high speed silver iodobromide emulsion (containing 4 mole% of silver iodide), which was then coated on a cellulose acetate film base and dried to obtain seven kinds of photographic materials each having a stable coating film which were designated Sample Nos. (13) to (19).

After exposure through an optical wedge, each sample was first developed at 21° C. for 12 minutes, using a developer of the following composition:
Composition of the developer:
  Metol: 3.0 g.
  Anhydrous sodium sulfite: 50.0 g.
  Hydroquinone: 6.0 g.
  Sodium carbonate: 40.0 g.
  Potassium bromide: 3.5 g.
  Potassium thiocyanate: 2.0 g.
  Water to make: 1,000 ml.

Subsequently, the developed sample was subjected to stopping, film-hardening and water-washing treatments according to ordinary procedures, thereafter to secondary exposure by use of a white light, and then to color development at 21° C. for 13 minutes, using a color developer of the following composition:
Composition of the color developer:
  N,N-Diethyl-2-methyl-p-phenylenediamine: 3.0 g.
  Anhydrous sodium sulfite: 4.0 g.
  Sodium carbonate: 20.0 g.
  Potassium bromide: 2.0 g.
  Water to make: 1,000 ml.

Thereafter, the sample was subjected to stopping, water-washing, bleaching and fixing treatments according to ordinary procedures, washed with running water for 20 minutes and then dried to form a yellow colored positive image on Samples (13), (14) and (17), a magenta colored positive image on Samples (15) and (18) and a cyan colored positive image on Samples (16) and (19), respectively.

The dye image formed in each sample was measured in speed, $D_{max}$, $\lambda_{max}$ and fastnesses to light and to heat-humidity. The results obtained were as set forth in Table 2.

In the table, the speed was represented by a relative value measured by assuming as 100 the speed of Sample (17) for yellow couplers, that of Sample (18) for magenta couplers and that of Sample (19) for cyan couplers, and the fastnesses were represented by percentages measured in the same manner as in Example 1.

Table 2

| Sample No. | Coupler | Speed | $D_{max}$ | $\lambda_{max}$ | Fastness Light fastness | Heat-humidity fastness |
|---|---|---|---|---|---|---|
| 13 | Coupler (8) | 133 | 2.42 | 457 | 92 | 97 |
| 14 | Coupler (14) | 125 | 2.26 | 456 | 93 | 97 |
| 15 | Coupler (30) | 130 | 2.46 | 540 | 94 | 97 |
| 16 | Coupler (53) | 137 | 2.60 | 683 | 97 | 96 |
| 17 | Control coupler (ii) | 100 | 2.14 | 455 | 85 | 95 |
| 18 | Control coupler (iii) | 100 | 2.24 | 557 | 81 | 73 |
| 19 | Control coupler (iv) | 100 | 2.30 | 680 | 93 | 90 |

As is clear from Table 2, the dye positive images formed in Samples (13) to (16), in which the couplers of the present invention had been used, were more excellent particularly in heat-humidity fastness than the image formed in Samples (17) to (19), in which the control coupler had been used, and the images were quite clear and were favorable in transparency.

EXAMPLE 4

A high speed silver iodobromide emulsion (containing 5 mole% of silver iodide) was coated on a polyester film base and then dried to prepare a light-sensitive photographic material having a single emulsion layer. This photographic material was exposed through an optical wedge, and then subjected to color development at 24° C. for 3 minutes, using an external type color developer of the below-mentioned composition which had been incorporated with the coupler (1).
Composition of the color developer:
N,N-Diethyl-2-methyl-p-phenylenediamine: 2.0 g.
Anhydrous sodium sulfite: 2.0 g.
Sodium carbonate (monohydrate): 20.0 g.
Potassium bromide: 1.0 g.
Coupler (1): 2.0 g.
Water to make: 1,000 ml.

Subsequently, the sample was washed with water for 4 minutes, treated with an ordinary bleaching bath for 5 minutes, washed with water for 5 minutes, fixed for 5 minutes, washed with water for 30 minutes and then dried to obtain a highly transparent yellow dye image having such excellent spectral absorption characteristic as an absorption maximum of 457 mμ.

What we claim is:

1. A method of processing an exposed light-sensitive silver halide color photographic material by a developer, which method comprises conducting said processing in the presence of a coupler represented by the following formula

wherein A is the residue of a coupler which is selected from the group consisting of benzoylacetanilide and pivaloylacetanilide yellow couplers, 1-phenyl-5-pyrazolone, indazolin-3-one and pyrazolo-benzimidazole magenta couplers, and phenol and naphthol cyan couplers; X is a biradical which is selected from the group consisting of

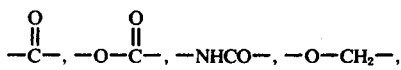

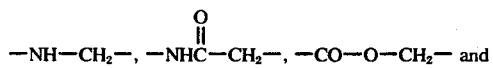

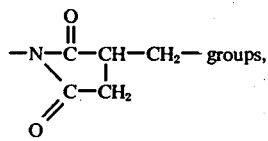

provided that the left bond of the group is attached to A while the right bond is connected to —$C_nF_{2n}H$; and n is an integer of 1 to 18 inclusive; further provided that X is not —NHCO— of which N is attached to A when the following three conditions are simultaneously met, one of the conditions being that A is a phenol or naphthol cyan coupler residue, another being that the hydrogen atom of —$C_nF_{2n}H$ is at the ω-position thereof, the other being that n is an even number of 2 to 14.

2. A method according to claim 1, wherein the photographic material comprises the coupler whereby the processing is carried out in the presence of the coupler.

3. A method according to claim 1, wherein the developer comprises the coupler whereby the processing is carried out in the presence of the coupler.

4. A light-sensitive silver halide color photographic emulsion which comprises a coupler represented by the following formula

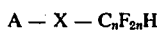

wherein A is the residue of a coupler which is selected from the group consisting of benzoylacetanilide and pivaloylacetanilide yellow couplers, 1-phenyl-5-pyrazolone, indazolin-3-one and pyrazolo-benzimidazole magenta couplers, and phenol and naphthol cyan couplers; X is a biradical which is selected from the group consisting of

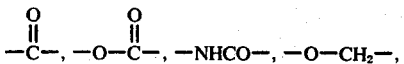

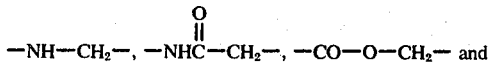

-continued

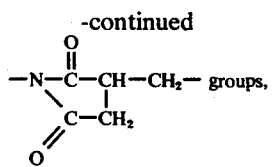
groups, provided that the left bond of the group is attached to A while the right bond is connected to $-C_nF_{2n}H$; and n is an integer of 1 to 18 inclusive; further provided that X is not $-NHCO-$ of which N is attached to A when the following three conditions are simultaneously met, one of the conditions being that A is a phenol or naphthol cyan coupler residue, another being that the hydrogen atom of $-C_nF_{2n}H$ is at the $\omega$-position thereof, the other being that $n$ is an even number of 2 to 14.

5. A color developer for developing an exposed light-sensitive silver halide color photographic material comprising a phenylenediamine-type developing agent and a coupler represented by the following formula $$A - X - C_nF_{2n}H$$

wherein A is the residue of a coupler which is selected from the group consisting of benzoylacetanilide and pivaloylacetanilide yellow couplers, 1-phenyl-5-pyrazolone, indazolin-3-one and pyrazolo-benzimidazole magenta couplers, and phenol and naphthol cyan couplers; X is a biradical which is selected from the group consisting of

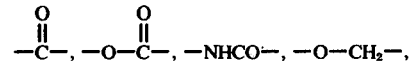

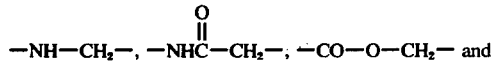

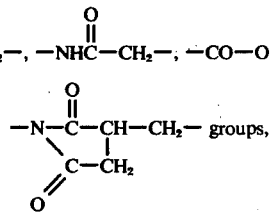
groups, provided that the left bond of the group is attached to A while the right bond is connected to $-C_nF_{2n}H$; and n is an integer of 1 to 18 inclusive; further provided that X is not $-NHCO-$ of which N is attached to A when the following three conditions are simultaneously met, one of the conditions being that A is a phenol or naphthol cyan coupler residue, another being that the hydrogen atom of $-C_nF_{2n}H$ is at the $\omega$-position thereof, the other being that $n$ is an even number of 2 to 14.

* * * * *